US010912728B2

(12) United States Patent
D'Arras et al.

(10) Patent No.: US 10,912,728 B2
(45) Date of Patent: *Feb. 9, 2021

(54) COSMETIC COMPOSITION CONTAINING LINEAR ALPHA-OLEFIN SULFONATES, ANIONIC SURFACTANTS, AND NON-IONIC AND/OR AMPHOTERIC SURFACTANTS, AND COSMETIC TREATMENT METHOD

(71) Applicant: L'OREAL, Paris (FR)

(72) Inventors: Marie-Florence D'Arras, Saint Ouen (FR); Lydia Dussault, Saint Ouen (FR); Estelle Mathonneau, Paris (FR); Gregory Plos, Paris (FR)

(73) Assignee: L'OREAL, Paris (FR)

( * ) Notice: Subject to any disclaimer, the term of this patent is extended or adjusted under 35 U.S.C. 154(b) by 350 days.

This patent is subject to a terminal disclaimer.

(21) Appl. No.: 15/535,124

(22) PCT Filed: Dec. 7, 2015

(86) PCT No.: PCT/FR2015/053342
§ 371 (c)(1),
(2) Date: Jun. 12, 2017

(87) PCT Pub. No.: WO2016/092188
PCT Pub. Date: Jun. 16, 2016

(65) Prior Publication Data
US 2017/0333323 A1 Nov. 23, 2017

(30) Foreign Application Priority Data
Dec. 12, 2014 (FR) .................................... 14 62309

(51) Int. Cl.
A61K 8/46 (2006.01)
A61K 8/44 (2006.01)
A61Q 5/02 (2006.01)
A61Q 19/10 (2006.01)

(52) U.S. Cl.
CPC ............... A61K 8/466 (2013.01); A61K 8/44 (2013.01); A61K 8/442 (2013.01); A61Q 5/02 (2013.01); A61Q 19/10 (2013.01)

(58) Field of Classification Search
None
See application file for complete search history.

(56) References Cited

U.S. PATENT DOCUMENTS

| 3,332,880 A * | 7/1967 | Kessler ............... C11D 1/14 510/327 |
| 3,472,840 A | 10/1969 | Stone et al. |
| 3,589,978 A | 6/1971 | Kamal et al. |
| 3,910,862 A | 10/1975 | Barabas et al. |
| 4,031,307 A | 6/1977 | DeMartino et al. |
| 4,131,576 A | 12/1978 | Iovine et al. |
| 4,165,367 A | 8/1979 | Chakrabarti |
| 4,223,009 A | 9/1980 | Chakrabrti |
| 5,955,066 A * | 9/1999 | Sako ..................... A61K 8/342 424/70.11 |
| 8,211,850 B2 | 7/2012 | Andjelic et al. |
| 10,561,592 B2 * | 2/2020 | Darras .................. A61K 8/442 |
| 2011/0158927 A1 | 6/2011 | Viravau et al. |
| 2015/0182437 A1 | 7/2015 | Mathonneau et al. |

FOREIGN PATENT DOCUMENTS

| EP | 0186507 A2 | 7/1986 |
| EP | 0342834 A2 | 11/1989 |
| FR | 1492597 A | 8/1967 |
| FR | 2077143 A5 | 10/1971 |
| FR | 2393573 A1 | 1/1979 |
| JP | H05-262638 A | 10/1993 |
| JP | 2001-181152 A | 7/2001 |
| JP | 2001-354514 A | 12/2001 |
| JP | 2006-282565 A | 10/2006 |
| WO | 2011/007174 A2 | 1/2011 |
| WO | 2016/092189 A1 | 6/2016 |

OTHER PUBLICATIONS

International Search Report for related PCT/FR2015/053344, dated Feb. 3, 2016.
International Search Report for counterpart PCT/FR2015/053342, dated Feb. 15, 2016.
Mintel: "Dry or Sensitised Skin Bar Soap," Galderma, XP002742929, Jul. 1, 2014.
Mintel: "Liquid Face & Body Cleanser," Sebapharma, XP002742930, Jun. 2, 2014.
Mintel: "Shampoo," Farouk Systems, XP002742915, Oct. 1, 2014.
Mintel: "Shampoo," Farouk Systems, XP002742914, Nov. 3, 2014.
Mintel: "Shampoo," Vogue International, XP002742928, Sep. 1, 2014.
Non-Final Office Action for co-pending U.S. Appl. No. 15/535,127, dated May 16, 2019.
Notice of Allowance for co-pending U.S. Appl. No. 15/535,127, dated Oct. 18, 2019.

(Continued)

Primary Examiner — Dominic Lazaro
(74) Attorney, Agent, or Firm — The Marbury Law Group, PLLC

(57) ABSTRACT

The invention relates to a cosmetic composition comprising:
one or more linear α-olefin sulfonates,
one or more anionic surfactants present in the composition in an amount ranging from 1% to 20% by weight; and
one or more additional surfactants chosen from amphoteric surfactants and nonionic surfactants,
the weight ratio of the amount of linear α-olefin sulfonates to the amount of anionic surfactants being greater than or equal to 1.
The invention also relates to a cosmetic treatment process using said composition, especially a process for caring for and/or cleansing keratin materials.

18 Claims, No Drawings

(56) References Cited

OTHER PUBLICATIONS

"Stepan's CocamideDEA Replacements for Personal Care," https://www.stepan.com/uploadedFiles/Literature_and_Downloads/General_Lit/Personal_Care/StepanCocamideDEAReplacementsPersonalCare.pdf.

* cited by examiner

COSMETIC COMPOSITION CONTAINING LINEAR ALPHA-OLEFIN SULFONATES, ANIONIC SURFACTANTS, AND NON-IONIC AND/OR AMPHOTERIC SURFACTANTS, AND COSMETIC TREATMENT METHOD

CROSS REFERENCE TO RELATED APPLICATIONS

This is a national stage application of PCT/FR2015/053342, filed internationally on Dec. 7, 2015, which claims priority to French Application No. 1462309, filed on Dec. 12, 2014, both of which are incorporated by reference herein in their entireties.

The present invention relates to a cosmetic composition comprising one or more linear α-olefin sulfonates, in combination with one or more additional anionic surfactants and with one or more additional surfactants chosen from amphoteric surfactants and nonionic surfactants; the invention also relates to a cosmetic treatment process using said composition.

Hair has a tendency to lose some of its qualities due to the action of factors especially such as natural regreasing, sweat, the removal of squamae, pollution or humidity. The visual appearance and the feel of the hair may thus be degraded. Regreasing, for example, makes the hair lank, and the hair then has a tendency to clump together. The hair may be more difficult to style, and may have an unpleasant greasy sheen or waxy feel. This is likewise the case for the skin, which has a tendency to lose some of its qualities due to the action of factors such as sweat, the removal of squamae, pollution, the climate and heating. The visual appearance may be degraded and thus lead to dull, dried-out skin, and a sensation of discomfort may appear.

It is common practice to use detergent cosmetic compositions such as shampoos or shower gels, based essentially on surfactants, for washing keratin materials such as the skin and the hair. These compositions are generally applied to the keratin materials, which are preferably wet, and the foam generated by massaging or rubbing with the hands or a washing mitt makes it possible, after rinsing with water, to remove the diverse types of soiling initially present on the hair or the skin. These compositions have substantial contents of detergent surfactants, which, in order to allow the formulation of cosmetic compositions with good washing power which are capable of removing soiling (sebum, sweat, pollution, etc.), squamae or dandruff, must especially give said compositions good foaming power. The surfactants that are useful for this purpose are generally of anionic, nonionic or amphoteric type, and particularly of anionic type.

The most common cosmetic compositions for washing keratin materials often contain anionic surfactants of sulfate type, which are very good detergent surfactants, but may prove to be relatively unfriendly to the keratin materials to be washed, in particular by having a drying effect on said materials, or even a negative impact on the conditioning of the hair or the skin. Specifically, gradually in the course of the applications, these surfactants may impair the cosmetic properties of the hair or the skin, thus leading to the need also to use conditioning agents such as cationic polymers, silicones or non-silicone oils. Sulfate surfactants may also give rise, in the case of certain sensitive consumers, to tolerance problems, especially on the skin and/or the eyes (stinging, tautness).

There is thus a need to propose cosmetic compositions, especially of shampoo or shower gel type, which have good detergent power and especially good foaming power, while at the same time being as free as possible of sulfate surfactants. However, cosmetic washing compositions that are free of sulfate surfactants must generally comprise large amounts of other surfactants in order to obtain the desired foam abundance and quality. However, the use of large amounts of these surfactants is undesirable, since it increases the cost of the compositions and may also lead to tolerance problems in the case of the most sensitive consumers.

Thus, there is a real need to provide cosmetic compositions which have satisfactory foam properties, without the need to use sulfate surfactants or large amounts of non-sulfate surfactants.

These compositions must also have good detergent or washing properties, and have good tolerance especially with respect to the skin, mucous membranes, the scalp and the eyes, while at the same time leading to good conditioning of keratin materials.

Finally, to avoid running on application and especially running into the eyes, detergent compositions of shampoo or shower gel type should, preferably, generally have a thickened texture, but without their thickening giving rise to problems of stability of the composition.

The Applicant has now discovered that a cosmetic composition containing a particular combination of surfactants makes it possible to achieve the objectives presented above.

One subject of the present invention is thus a cosmetic composition comprising:
 (i) one or more linear α-olefin sulfonates,
 (ii) one or more anionic surfactants other than the compounds (i), present in the composition in an amount ranging from 1% to 20% by weight relative to the total weight of the composition; and
 (iii) one or more additional surfactants chosen from amphoteric surfactants and nonionic surfactants,
the weight ratio of the amount of linear α-olefin sulfonates (i) to the amount of anionic surfactants (ii) other than the compounds (i) being greater than or equal to 1 (weight ratio (i)/(ii)≥1).

The compositions according to the invention allow the production of an abundant foam of very good quality, which is especially creamy, this production being rapid. They especially provide a homogeneous foam which has good persistence over time. The foam formed from the composition according to the invention spreads easily and uniformly on keratin materials.

The present invention makes it possible to obtain optimum foaming performance when compared with the amount of non-sulfate surfactants present in the composition. Thus, the present invention makes it possible to formulate compositions which, for a surfactant content equivalent to that of the compositions of the prior art, have superior foaming performance. Above all, the present invention makes it possible to formulate compositions that may contain smaller amounts of surfactants than the compositions of the prior art, while at the same time having at least equivalent or even superior foaming performance.

In addition, the composition according to the invention has good cosmetic properties, and especially affords good conditioning of keratin materials and especially of the hair, including when they are sensitized.

The composition according to the invention may also have a thickened texture, which allows it to be spread on the hair while avoiding running into the eyes, for example; it has also been found that the composition according to the invention is particularly stable, even though of thickened texture.

By implementing the invention, it is thus possible to obtain thickened foaming compositions without the need to add thickeners other than salt (for example NaCl), which might harm the stability of said composition and/or its foaming properties.

Preferably, the composition according to the invention has a viscosity, measured at 25° C. and 1 atm., of between 1 and 20 Pa·s, better still between 3 and 15 Pa·s and most particularly between 4 and 12 Pa·s.

The viscosity is preferably measured using a Haake Mars rheometer in cone-plate geometry, with a diameter of 60 mm/1° (titanium). The temperature is regulated by a Peltier-effect plane at 25° C., and the shear rate is 200 s$^{-1}$. The viscosity may also be measured using a Rheomat 180 machine at 25° C. and 1 atm., with a 3 or 4 spindle, the spin speed being 200 rpm and the measuring time 10 minutes, the shear rate being 200 s$^{-1}$.

In the present description, the expression "at least one" is equivalent to the expression "one or more" and can be replaced therewith.

In the present description, the expression "between" is equivalent to the expression "ranging from" and can be replaced therewith; in these expressions, the limits are considered as being included.

(I) Linear α-Olefin Sulfonates (or Linear Alpha-Olefin Sulfonates)

The cosmetic composition according to the invention thus comprises one or more linear α-olefin sulfonates, preferably comprising 8 to 28 carbon atoms, especially from 10 to 24 carbon atoms, better still from 12 to 20 carbon atoms and in particular from 14 to 18 carbon atoms.

Said α-olefin sulfonates are known compounds and are described especially in Ullmann's Encyclopedia of Industrial Chemistry or in U.S. Pat. No. 8,211,850. These compounds are generally obtained by sulfonation of long-chain α-olefins.

The linear α-olefin sulfonates according to the invention generally comprise, in a known manner, a mixture of linear alkene sulfonates, especially of formula (A), optionally as a mixture with linear hydroxyalkane sulfonates, especially of formula (B).

Said linear alkene sulfonates may thus be of formula (A):

R—CH$_2$—CH=CH—(CH$_2$)$n$—SO$_3$M in which:
R is a saturated linear alkyl radical comprising from 4 to 30 carbon atoms, especially from 6 to 20 carbon atoms, or even from 8 to 18 carbon atoms and better still from 10 to 14 carbon atoms;
n is an integer between 0 and 10, preferably between 1 and 4 and better still n=1;
M is a cosmetically acceptable cation, chosen especially from the ammonium cation, cations derived from alkali metals or alkaline-earth metals, cations derived from organic amines such as alkanolamines; preferably those derived from alkali metals; and especially Na+ or K+.

Preferably, R represents a linear alkyl radical comprising from 8 to 14 carbon atoms, especially from 10 to 12 carbon atoms.

Preferably, M is derived from an alkali metal, especially Na+ or K+.

Preferably, the linear alkene sulfonates according to the invention have the formula:

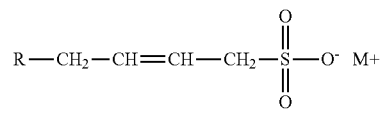

in which:
R is a saturated linear alkyl radical comprising from 4 to 20 carbon atoms, especially from 6 to 18 carbon atoms, or even from 8 to 14 carbon atoms and better still from 10 to 12 carbon atoms;
M is a cosmetically acceptable cation, chosen especially from the ammonium cation, cations derived from alkali metals or alkaline-earth metals, cations derived from organic amines such as alkanolamines; preferably those derived from alkali metals or alkali metals; and especially Na+ or K+.

The linear hydroxyalkane sulfonates may be of formula (B):

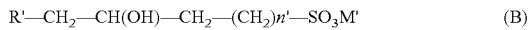

R'—CH$_2$—CH(OH)—CH$_2$—(CH$_2$)$n'$—SO$_3$M'     (B)

in which:
R' is a saturated linear alkyl radical comprising from 4 to 30 carbon atoms, especially from 6 to 20 carbon atoms, or even from 8 to 18 carbon atoms and better still from 10 to 14 carbon atoms;
n' is an integer between 0 and 10, preferably between 1 and 4 and better still n'=1;
M' is a cosmetically acceptable cation, chosen especially from the ammonium cation, cations derived from alkali metals or alkaline-earth metals, cations derived from organic amines such as alkanolamines; preferably those derived from alkali metals; and especially Na+ or K+.

Preferably, R' represents a linear alkyl radical comprising from 8 to 14 carbon atoms, especially from 10 to 12 carbon atoms.

Preferably, M' is derived from an alkali metal, especially Na+ or K+.

Preferably, the linear hydroxyalkane sulfonates have the formula:

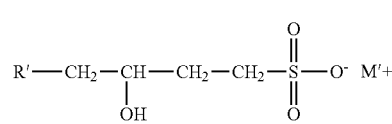

in which:
R' is a saturated linear alkyl radical comprising from 4 to 20 carbon atoms, especially from 6 to 18 carbon atoms, or even from 8 to 14 carbon atoms and better still from 10 to 12 carbon atoms;
M' is a cosmetically acceptable cation, chosen especially from the ammonium cation, cations derived from alkali metals or alkaline-earth metals, cations derived from organic amines such as alkanolamines; preferably those derived from alkali metals or alkali metals; and especially Na+ or K+.

Preferably, R and R' are identical.
Preferably, M and M' are identical.
Preferably, the linear α-olefin sulfonates according to the invention are chosen from linear α-olefin sulfonates comprising 8 to 28 carbon atoms, especially from 10 to 24 carbon atoms, better still from 12 to 20 carbon atoms, in particular from 14 to 18 carbon atoms; in particular of alkali metals, especially of sodium.

Commercial products that may especially be mentioned include those sold under the name Bio-Terge AS-40A or Bio-Terge AS-40HA by the company Stepan, or Calsoft AOS-40 by the company Pilot Chemical, or alternatively Nansa LSS38/AV by the company Huntsman.

Preferably, the cosmetic composition according to the invention comprises said linear α-olefin sulfonates in an amount ranging from 1% to 20% by weight, especially from 4% to 18% by weight and preferably from 6% to 16% by weight, relative to the total weight of the cosmetic composition.

(ii) Additional Anionic Surfactants

The composition according to the invention also comprises one or more anionic surfactants other than the linear α-olefin sulfonate surfactants above.

The term "anionic surfactant" means a surfactant comprising, as ionic or ionizable groups, only anionic groups.

In the present description, a species is termed "anionic" when it bears at least one permanent negative charge or when it can be ionized into a negatively charged species, under the conditions of use of the composition of the invention (for example the medium or the pH) and not comprising any cationic charge.

Said additional anionic surfactants are preferably chosen from sulfonate surfactants and carboxylate surfactants. Needless to say, a mixture of these surfactants may be used.

It is understood in the present description that:
the carboxylate anionic surfactants comprise at least one carboxylic or carboxylate function (—COOH or —COO—) and may optionally also comprise one or more sulfate and/or sulfonate functions;
the sulfonate anionic surfactants comprise at least one sulfonate function (—SO$_3$H or —SO$_3$—) and may optionally also comprise one or more sulfate functions, but do not comprise any carboxylate functions.

The carboxylic anionic surfactants that may be used thus comprise at least one carboxylic or carboxylate function (—COOH or —COO—).

They may be chosen from the following compounds: acylglycinates, acyllactylates, acylsarcosinates, acylglutamates; alkyl ether carboxylic acids, alkyl(C$_{6-30}$ aryl) ether carboxylic acids, alkylamido ether carboxylic acids; and also the salts of these compounds;
the alkyl and/or acyl groups of these compounds comprising from 6 to 30 carbon atoms, especially from 12 to 28, better still from 14 to 24 or even from 16 to 22, carbon atoms; the aryl group preferably denoting a phenyl or benzyl group; these compounds possibly being polyoxyalkylenated, especially polyoxyethylenated, and then preferably comprising from 1 to 50 ethylene oxide units, better still from 2 to 10 ethylene oxide units.

The sulfonate anionic surfactants, other than the compounds (i), that may be used comprise at least one sulfonate function (—SO$_3$H or —SO$_3$$^-$).

They may be chosen from the following compounds: alkylsulfonates, alkylamidesulfonates, alkylarylsulfonates, paraffin sulfonates, alkylsulfosuccinates, alkyl ether sulfosuccinates, alkylamidesulfosuccinates, alkylsulfoacetates, N-acyltaurates, acylisethionates; alkylsulfolaurates; and also the salts of these compounds;
the alkyl groups of these compounds comprising from 6 to 30 carbon atoms, especially from 12 to 28, better still from 14 to 24 or even from 16 to 22, carbon atoms; the aryl group preferably denoting a phenyl or benzyl group; these compounds possibly being polyoxyalkylenated, in particular polyoxyethylenated, and then preferably comprising from 1 to 50 ethylene oxide units and better still from 2 to 10 ethylene oxide units.

When the anionic surfactant is in salt form, said salt may be chosen from alkali metal salts, such as the sodium or potassium salt, ammonium salts, amine salts and in particular amino alcohol salts, and alkaline-earth metal salts, such as the magnesium salt. Examples of amino alcohol salts that may be mentioned include monoethanolamine, diethanolamine and triethanolamine salts, monoisopropanolamine, diisopropanolamine or triisopropanolamine salts, 2-amino-2-methyl-1-propanol salts, 2-amino-2-methyl-1,3-propanediol salts and tris(hydroxymethyl)aminomethane salts. Alkali metal or alkaline-earth metal salts and in particular the sodium or magnesium salts are preferably used.

Preferentially, said anionic surfactants are chosen, alone or as a mixture, from:
acylglutamates, especially of C$_6$-C$_{24}$ or even C$_{12}$-C$_{20}$, such as stearoylglutamates, and in particular disodium stearoylglutamate;
acylsarcosinates, especially of C$_6$-C$_{24}$ or even C$_{12}$-C$_{20}$, such as palmitoylsarcosinates and lauroylsarcosinates, and in particular sodium palmitoylsarcosinate or sodium lauroylsarcosinate;
acyllactylates, especially of C$_{12}$-C$_{28}$ or even C$_{14}$-C$_{24}$, such as behenoyllactylates, and in particular sodium behenoyllactylate;
C$_6$-C$_{24}$ and especially C$_{12}$-C$_{20}$ acylglycinates;
C$_6$-C$_{24}$ and especially C$_{12}$-C$_{20}$ N-acyltaurates;
(C$_6$-C$_{24}$)alkyl ether carboxylates and especially (C$_{12}$-C$_{20}$) alkyl ether carboxylates;
polyoxyalkylenated (C$_6$-C$_{24}$)alkyl amido ether carboxylic acids, in particular those comprising from 2 to 50 ethylene oxide groups;
C$_6$-C$_{24}$ and especially C$_{12}$-C$_{20}$ alkylsulfosuccinates, especially laurylsulfosuccinates, in particular of sodium;
C$_6$-C$_{24}$ and especially C$_{12}$-C$_{20}$ alkylethersulfosuccinates, especially laurylsulfosuccinates, which are oxyethylenated, especially with 3 EO, especially of sodium;
(C$_6$-C$_{24}$)acylisethionates, preferably (C$_{12}$-C$_{18}$)acylisethionates, and most particularly cocoylisethionates, especially of sodium;
C$_6$-C$_{24}$ and especially C$_{12}$-C$_{20}$ alkylsulfoacetates;
in particular in the form of alkali metal or alkaline-earth metal, ammonium or amino alcohol salts.

Even more preferentially, said anionic surfactants are chosen, alone or as a mixture, from:
acylsarcosinates, especially of C$_6$-C$_{24}$ or even C$_{12}$-C$_{20}$, such as palmitoylsarcosinates and lauroylsarcosinates, and in particular sodium palmitoylsarcosinate or sodium lauroylsarcosinate;
C$_6$-C$_{24}$ and in particular C$_{12}$-C$_{20}$ alkylsulfosuccinates, especially laurylsulfosuccinates, in particular of sodium;
(C$_6$-C$_{24}$)acylisethionates, preferably (C$_{12}$-C$_{18}$)acylisethionates, and most particularly cocoylisethionates, especially of sodium;
C$_6$-C$_{24}$ and especially C$_{12}$-C$_{20}$ alkylsulfoacetates;
C$_6$-C$_{24}$ and especially C$_{12}$-C$_{20}$ N-acyltaurates;
in particular in the form of alkali metal or alkaline-earth metal, ammonium or amino alcohol salts.

The anionic surfactant(s) other than the compounds (i) are present in the composition in an amount ranging from 1% to 20% by weight, especially from 1.5% to 15% by weight, better still from 2% to 10% by weight and even better still from 3% to 10% by weight, relative to the total weight of the composition.

In addition, the weight ratio of the amount of linear α-olefin sulfonates (i) to the amount of anionic surfactants (ii) other than the compounds (i) is greater than or equal to 1 (weight ratio (i)/(ii)≥1), preferably between 1.2 and 12, especially between 1.5 and 10, or even between 1.8 and 8, better still ranging from 2 to 7, or even from 2 to 4.

Preferably, the composition according to the invention is said to be "sulfate-free", i.e. it does not comprise any (0%) anionic surfactants comprising sulfate groups, for instance alkyl sulfates and alkyl ether sulfates.

(iii) Additional Nonionic and Amphoteric Surfactants

The composition according to the invention also comprises one or more additional surfactants chosen from nonionic surfactants and amphoteric surfactants.

The nonionic surfactants that may be used may be chosen from alcohols, α-diols and ($C_{1-20}$)alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; and/or these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably having from 2 to 30 ethylene oxide units, polyglycerolated fatty amides comprising on average from to 5, and in particular from 1.5 to 4, glycerol groups; $C_8$-$C_{30}$ fatty acid alkanolamides, such as $C_8$-$C_{30}$ fatty acid monoalkanolamides, in particular $C_8$-$C_{30}$ fatty acid monoethanolamides or monoisopropanolamides; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—($C_{6-24}$ alkyl)glucamine derivatives, amine oxides such as ($C_{10-14}$ alkyl)amine oxides or N—($C_{10-14}$ acyl)aminopropylmorpholine oxides.

Mention may also be made of nonionic surfactants of alkylpolyglycoside type, represented especially by the following general formula:

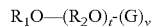

in which:
R₁ represents a linear or branched alkyl or alkenyl radical comprising 6 to 24 carbon atoms and especially 8 to 18 carbon atoms, or an alkylphenyl radical whose linear or branched alkyl radical comprises 6 to 24 carbon atoms and especially 8 to 18 carbon atoms;
R₂ represents an alkylene radical comprising 2 to 4 carbon atoms,
G represents a sugar unit comprising 5 to 6 carbon atoms,
t denotes a value ranging from 0 to 10 and preferably 0 to 4,
v denotes a value ranging from 1 to 15 and preferably 1 to 4.

Preferably, the alkylpolyglycoside surfactants are compounds of the formula described above in which:
R₁ denotes a linear or branched, saturated or unsaturated alkyl radical comprising from 8 to 18 carbon atoms,
R₂ represents an alkylene radical comprising 2 to 4 carbon atoms, t denotes a value ranging from 0 to 3 and preferably equal to 0,
G denotes glucose, fructose or galactose, preferably glucose;
the degree of polymerization, i.e. the value of v, possibly ranging from 1 to 15 and preferably from 1 to 4; the mean degree of polymerization more particularly being between 1 and 2.

The glucoside bonds between the sugar units are generally of 1-6 or 1-4 type and preferably of 1-4 type. Preferably, the alkylpolyglycoside surfactant is an alkylpolyglucoside surfactant. $C_8$/$C_{16}$ alkyl polyglycosides 1,4, and especially decyl glucosides and caprylyl/capryl glucosides, are most particularly preferred.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or else the products sold by the company Chem Y under the name AG10 LK.

Preferably, use is made of $C_8$/$C_{16}$-alkyl polyglycosides 1,4, especially as an aqueous 53% solution, such as those sold by Cognis under the reference Plantacare® 818 UP.

Preferentially, the nonionic surfactants are chosen from ($C_{6-24}$ alkyl)polyglycosides, and more particularly ($C_{8-18}$ alkyl)polyglycosides, ethoxylated $C_8$-$C_{30}$ fatty acid esters of sorbitan, polyethoxylated $C_8$-$C_{30}$ fatty alcohols, polyoxyethylenated $C_8$-$C_{30}$ fatty acid esters, these compounds preferably containing from 2 to 150 mol of ethylene oxide, and $C_8$-$C_{30}$ fatty acid alkanolamides such as $C_8$-$C_{30}$ fatty acid monoalkanolamides, in particular $C_8$-$C_{30}$ fatty acid monoethanolamides or monoisopropanolamides, and mixtures thereof.

The amphoteric surfactants that may be used in the invention may be optionally quaternized secondary or tertiary aliphatic amine derivatives, in which the aliphatic group is a linear or branched chain comprising from 8 to 22 carbon atoms, said amine derivatives containing at least one anionic group, for instance a carboxylate, sulfonate, sulfate, phosphate or phosphonate group.

Mention may be made in particular of ($C_8$-$C_{20}$)alkylbetaines, sulfobetaines, ($C_8$-$C_{20}$)alkylsulfobetaines, ($C_8$-$C_{20}$)alkylamido($C_1$-$C_6$)alkylbetaines, such as cocamidopropylbetaine, ($C_8$-$C_{20}$)alkylamido($C_1$-$C_6$)alkylsulfobetaines, and also mixtures thereof.

Among the optionally quaternized secondary or tertiary aliphatic amine derivatives that may be used, mention may also be made of the products having the following respective structures (A1) and (A2):

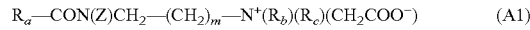

in which:
$R_a$ represents a $C_{10}$-$C_{30}$ alkyl or alkenyl group derived from an acid $R_a$—COOH preferably present in hydrolyzed coconut oil, or a heptyl, nonyl or undecyl group,
$R_b$ represents a β-hydroxyethyl group,
$R_c$ represents a carboxymethyl group;
m is equal to 0, 1 or 2,
Z represents a hydrogen atom or a hydroxyethyl or carboxymethyl group,

in which:

B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom, B' represents —(CH$_2$)$_z$—Y', with z=1 or 2, and Y' representing —COOH, —COOZ', —CH$_2$—CHOH—SO$_3$H or —CH$_2$—CHOH—SO$_3$Z', m' is equal to 0, 1 or 2, Z represents a hydrogen atom or a hydroxyethyl or carboxymethyl group, Z' represents an ion derived from an alkali metal or alkaline-earth metal, such as sodium, potassium or magnesium; an ammonium ion; or an ion derived from an organic amine and especially from an amino alcohol, such as monoethanolamine, diethanolamine and triethanolamine, monoisopropanolamine, diisopropanolamine or triisopropanolamine, 2-amino-2-methyl-1-propanol, 2-amino-2-methyl-1,3-propanediol and tris(hydroxymethyl)aminomethane.

R$_{a'}$ represents a C$_{10}$-C$_{30}$ alkyl or alkenyl group of an acid R$_a$COOH preferably present in hydrolyzed linseed oil or coconut oil, an alkyl group, especially a C$_{17}$ alkyl group, and its iso form, or an unsaturated C$_{17}$ group.

The compounds corresponding to formula (A2) are particularly preferred.

Among the compounds of formula (A2) for which X' represents a hydrogen atom, mention may be made of the compounds known under the (CTFA) names sodium cocoamphoacetate, sodium lauroamphoacetate, sodium caproamphoacetate and sodium capryloamphoacetate.

Other compounds of formula (A2) are known under the (CTFA) names disodium cocoamphodiacetate, disodium lauroamphodiacetate, disodium caproamphodiacetate, disodium capryloamphodiacetate, disodium cocoamphodipropionate, disodium lauroamphodipropionate, disodium caproamphodipropionate, disodium capryloamphodipropionate, lauroamphodipropionic acid and cocoamphodipropionic acid.

As examples of compounds of formula (A2), mention may be made of the cocoamphodiacetate sold by the company Rhodia under the trade name Miranol® C2M Concentrate, the sodium cocoamphoacetate sold under the trade name Miranol Ultra C 32 and the product sold by the company Chimex under the trade name Chimexane HA.

Use may also be made of compounds of formula (A3):

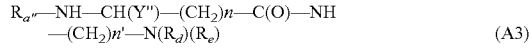

$$R_{a''}\text{—NH—CH(Y'')—(CH}_2)n\text{—C(O)—NH}$$
$$\text{—(CH}_2)n'\text{—N(R}_d)(R_e) \qquad (A3)$$

in which:

R$_{a''}$ represents a C$_{10}$-C$_{30}$ alkyl or alkenyl group of an acid R$_{a''}$—C(O)OH, which is preferably present in hydrolyzed linseed oil or coconut oil;

Y''' represents the group —C(O)OH, —C(O)OZ'', —CH$_2$—CH(OH)—SO$_3$H or the group —CH$_2$—CH(OH)—SO$_3$—Z'', with Z'' representing a cation resulting from an alkali metal or alkaline-earth metal, such as sodium, an ammonium ion or an ion resulting from an organic amine;

R$_d$ and R$_e$, independently of each other, represent a C$_1$-C$_4$ alkyl or hydroxyalkyl radical; and n and n', independently of each other, denote an integer ranging from 1 to 3.

Among the compounds of formula (A3), mention may in particular be made of the compound classified in the CTFA dictionary under the name sodium diethylaminopropyl cocoaspartamide and in particular the compound sold by the company Chimex under the name Chimexane HB.

Preferably, the amphoteric surfactants are chosen from (C$_8$-C$_{20}$)alkylbetaines, (C$_8$-C$_{20}$)alkylamido(C$_1$-C$_6$)alkylbetaines, (C$_8$-C$_{20}$)alkylamphoacetates and (C$_8$-C$_{20}$)alkylamphodiacetates, and mixtures thereof.

According to a particular embodiment of the invention, the cosmetic composition comprises at least one nonionic surfactant and at least one amphoteric surfactant. Preferentially, in this embodiment, the nonionic surfactant is chosen from (C$_{6-24}$ alkyl)polyglycosides, and more particularly (C$_{8-18}$ alkyl)polyglycosides, ethoxylated C$_8$-C$_{30}$ fatty acid esters of sorbitan, polyethoxylated C$_7$-C$_{30}$ fatty alcohols and polyoxyethylenated C$_8$-C$_{30}$ fatty acid esters, these compounds preferably containing from 2 to 150 mol of ethylene oxide, C$_8$-C$_{30}$ fatty acid alkanolamides such as C$_8$-C$_{30}$ fatty acid monoalkanolamides, in particular C$_8$-C$_{30}$ fatty acid monoethanolamides or monoisopropanolamides, and mixtures thereof; and better still the nonionic surfactant is chosen from C$_8$-C$_{30}$ fatty acid alkanolamides, such as C$_8$-C$_{30}$ fatty acid monoalkanolamides, in particular C$_8$-C$_{30}$ fatty acid monoethanolamides or monoisopropanolamides.

Preferentially, in this embodiment, the amphoteric surfactants are chosen from (C$_8$-C$_{20}$)alkylbetaines, (C$_8$-C$_{20}$)alkylamido(C$_1$-C$_6$)alkylbetaines, (C$_8$-C$_{20}$)alkylamphoacetates and (C$_8$-C$_{20}$)alkylamphodiacetates, and mixtures thereof.

The composition according to the invention preferably comprises said additional nonionic and/or amphoteric surfactant(s) in a total amount ranging from 0.5% to 20% by weight, especially from 1% to 15% by weight, preferentially from 1.5% to 12% by weight or even from 2% to 10% by weight, relative to the total weight of the composition.

Preferably, the composition according to the invention comprises one or more amphoteric surfactants, which are preferably present in an amount ranging from 0.5% to 15% by weight, especially from 1% to 10% by weight and preferentially from 1.5% to 8% by weight, relative to the total weight of the composition.

In one particular embodiment, the composition according to the invention comprises a total content of surfactants (linear olefin sulfonates (i)+anionic surfactants (ii)+amphoteric surfactants and nonionic surfactants (iii)+cationic surfactants, where appropriate) of less than or equal to 25% by weight, in particular less than or equal to 22% by weight, especially less than or equal to 20% by weight, and better still less than or equal to 18% by weight, relative to the total weight of said composition.

Electrolyte

The composition according to the invention may also comprise one or more electrolytes chosen, for example, from mineral salts of alkali metals or alkaline-earth metals, such as sodium chloride, sodium sulfate, magnesium chloride, magnesium sulfate, and even more preferentially chosen from mineral salts of monovalent alkali metals or alkaline-earth metals, and in particular sodium chloride.

The composition according to the invention preferably comprises said electrolyte(s) in an amount ranging from 0.01% to 10% by weight, especially from 0.05% to 5% by weight, better still from 0.1% to 3% by weight or even from 0.15% to 2% by weight, relative to the total weight of the composition.

Amphoteric or Cationic Polymers

The composition according to the invention may also comprise one or more polymers chosen from amphoteric or cationic polymers, and also mixtures thereof.

The term "cationic polymer" means any polymer comprising cationic groups and/or groups that can be ionized to cationic groups. Preferably, the cationic polymer is hydrophilic or amphiphilic. The preferred cationic polymers are chosen from those that contain units comprising primary, secondary, tertiary and/or quaternary amine groups that may either form part of the main polymer chain or may be borne by a side substituent directly connected thereto.

The cationic polymers that may be used preferably have a weight-average molar mass (Mw) of between 500 and $5 \times 10^6$ approximately and preferably between $10^3$ and $3 \times 10^6$ approximately.

Among the cationic polymers, mention may be made more particularly of:

(1) homopolymers or copolymers derived from acrylic or methacrylic esters or amides and comprising at least one of the units of the following formulae:

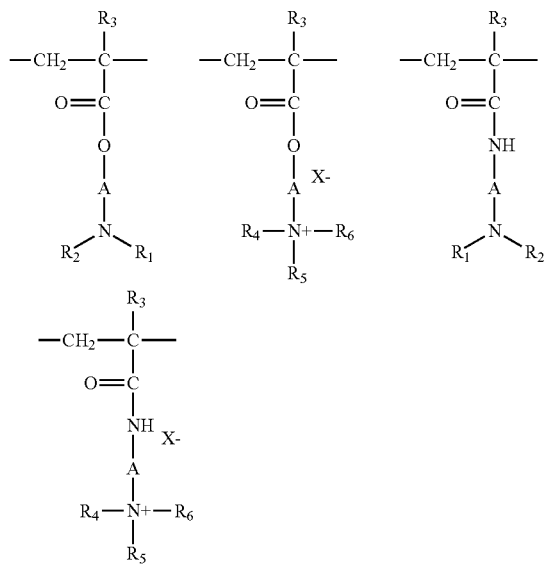

in which:
- $R_3$, which may be identical or different, denote a hydrogen atom or a $CH_3$ radical;
- A, which may be identical or different, represent a linear or branched divalent alkyl group of 1 to 6 carbon atoms, preferably 2 or 3 carbon atoms, or a hydroxyalkyl group of 1 to 4 carbon atoms;
- $R_4$, $R_5$ and $R_6$, which may be identical or different, represent an alkyl group containing from 1 to 18 carbon atoms or a benzyl radical, preferably an alkyl group containing from 1 to 6 carbon atoms;
- $R_1$ and $R_2$, which may be identical or different, represent a hydrogen atom or an alkyl group containing from 1 to 6 carbon atoms, preferably methyl or ethyl;
- X denotes an anion derived from a mineral or organic acid, such as a methosulfate anion or a halide such as chloride or bromide.

The copolymers of family (1) may also contain one or more units derived from comonomers that may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Among these copolymers of family (1), mention may be made of:
- copolymers of acrylamide and of dimethylaminoethyl methacrylate quaternized with dimethyl sulfate or with a dimethyl halide, such as that sold under the name Hercofloc by the company Hercules,
- copolymers of acrylamide and of methacryloyloxyethyltrimethylammonium chloride, such as the products sold under the name Bina Quat P 100 by the company Ciba Geigy,
- the copolymer of acrylamide and of methacryloyloxyethyltrimethylammonium methosulfate, such as that sold under the name Reten by the company Hercules,
- quaternized or non-quaternized vinylpyrrolidone/dialkylaminoalkyl acrylate or methacrylate copolymers, such as the products sold under the name Gafquat by the company ISP, for instance Gafquat 734 or Gafquat 755, or alternatively the products known as Copolymer 845, 958 and 937. These polymers are described in detail in French patents 2,077,143 and 2,393,573,
- dimethylaminoethyl methacrylate/vinylcaprolactam/vinylpyrrolidone terpolymers, such as the product sold under the name Gaffix VC 713 by the company ISP,
- vinylpyrrolidone/methacrylamidopropyldimethylamine copolymers, such as the copolymers sold under the name Styleze CC 10 by ISP,
- vinylpyrrolidone/quaternized dimethylaminopropylmethacrylamide copolymers such as the product sold under the name Gafquat HS 100 by the company ISP,
- preferably crosslinked polymers of methacryloyloxy($C_1$-$C_4$)alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, in particular methylenebisacrylamide. Use may be made more particularly of a crosslinked acrylamide/methacryloyloxyethyltrimethylammonium chloride copolymer (20/80 by weight) in the form of a dispersion comprising 50% by weight of said copolymer in mineral oil. This dispersion is sold under the name Salcare® SC 92 by the company Ciba. Use may also be made of a crosslinked methacryloyloxyethyltrimethylammonium chloride homopolymer comprising approximately 50% by weight of the homopolymer in mineral oil or in a liquid ester. These dispersions are sold under the names Salcare® SC 95 and Salcare® SC 96 by the company Ciba.

(2) cationic polysaccharides, especially cationic galactomannan gums and celluloses. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are in particular described in FR1,492, 597, and mention may be made of the polymers sold under the name Ucare Polymer JR (JR 400 LT, JR 125 and JR 30M) or LR (LR 400 and LR 30M) by the company Amerchol. These polymers are also defined in the CTFA dictionary as quaternary ammoniums of hydroxyethylcellulose that have reacted with an epoxide substituted with a trimethylammonium group.

Cationic cellulose copolymers or cellulose derivatives grafted with a water-soluble quaternary ammonium monomer are described in particular in U.S. Pat. No. 4,131,576, and mention may be made of hydroxyalkyl celluloses, for instance hydroxymethyl-, hydroxyethyl- or hydroxypropyl-celluloses grafted, in particular, with a methacryloylethyltrimethylammonium, methacrylamidopropyltrimethylammonium or dimethyldiallylammonium salt. The commercial products corresponding to this definition are more particularly the products sold under the names Celquat L 200 and Celquat H 100 by the company National Starch.

The cationic galactomannan gums are described more particularly in U.S. Pat. Nos. 3,589,578 and 4,031,307, and mention may be made of guar gums comprising cationic trialkylammonium groups. Use is made, for example, of guar gums modified with a 2,3-epoxypropyltrimethylammonium salt (for example, chloride). Such products are in particular sold under the names Jaguar C13 S, Jaguar C 15, Jaguar C 17 and Jaguar C162 by the company Rhodia.

(3) polymers formed from piperazinyl units and divalent alkylene or hydroxyalkylene radicals containing linear or branched chains, optionally interrupted with oxygen, sulfur or nitrogen atoms or with aromatic or heterocyclic rings, and also the oxidation and/or quaternization products of these polymers.

(4) water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized.

(5) polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Among these derivatives, mention may be made more particularly of the adipic acid/dimethylaminohydroxypropyl/diethylenetriamine polymers sold under the name Cartaretine F, F4 or F8 by the company Sandoz.

(6) polymers obtained by reacting a polyalkylene polyamine comprising two primary amine groups and at least one secondary amine group with a dicarboxylic acid chosen from diglycolic acid and saturated aliphatic dicarboxylic acids containing from 3 to 8 carbon atoms; the mole ratio between the polyalkylene polyamine and the dicarboxylic acid preferably being between 0.8:1 and 1.4:1; the resulting polyamino amide being reacted with epichlorohydrin in a mole ratio of epichlorohydrin relative to the secondary amine group of the polyaminoamide preferably of between 0.5:1 and 1.8:1. Polymers of this type are sold in particular under the name Hercosett 57 by Hercules Inc. or else under the name PD 170 or Delsette 101 by Hercules in the case of the adipic acid/epoxypropyl/diethylenetriamine copolymer.

(7) cyclopolymers of alkyldiallylamine or of dialkyldiallylammonium, such as the homopolymers or copolymers containing, as main constituent of the chain, units corresponding to formula (I) or (II):

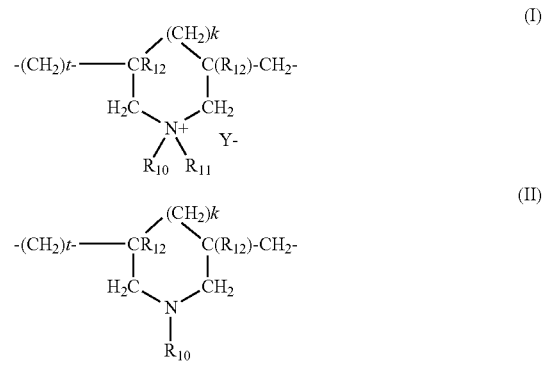

in which
k and t are equal to 0 or 1, the sum k+t being equal to 1;
$R_{12}$ denotes a hydrogen atom or a methyl radical;
$R_{10}$ and $R_{11}$, independently of each other, denote an alkyl group containing from 1 to 6 carbon atoms, a hydroxyalkyl group in which the alkyl group contains 1 to 5 carbon atoms, a $C_1$-$C_4$ amidoalkyl group; or alternatively $R_{10}$ and $R_{11}$ may denote, together with the nitrogen atom to which they are attached, heterocyclic groups such as piperidyl or morpholinyl; $R_{10}$ and $R_{11}$, independently of each other, preferably denote an alkyl group containing from 1 to 4 carbon atoms;
$Y^-$ is an anion such as bromide, chloride, acetate, borate, citrate, tartrate, bisulfate, bisulfite, sulfate or phosphate.

Mention may be made more particularly of the dimethyldiallylammonium salts (for example chloride) homopolymer for example sold under the name Merquat 100 by the company Nalco (and homologs thereof of low weight-average molar masses) and the copolymers of diallyldimethylammonium and acrylamide salts (for example chloride), sold in particular under the name Merquat 550 or Merquat 7SPR.

(8) quaternary diammonium polymers comprising repeating units of formula:

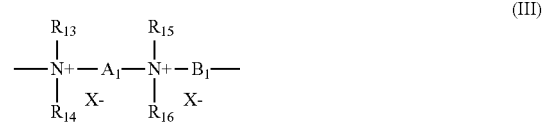

in which:
$R_{13}$, $R_{14}$, $R_{15}$ and $R_{16}$, which may be identical or different, represent aliphatic, alicyclic or arylaliphatic radicals comprising from 1 to 20 carbon atoms, or lower hydroxyalkylaliphatic radicals, or else $R_{13}$, $R_{14}$, $R_{15}$ and $R_{16}$, together or separately, constitute, with the nitrogen atoms to which they are attached, heterocycles optionally comprising a second non-nitrogen heteroatom, or else $R_{13}$, $R_{14}$, $R_{15}$ and $R_{16}$ represent a linear or branched $C_1$-$C_6$ alkyl radical substituted with a nitrile, ester, acyl, amide or —CO—O—$R_{17}$-D or —CO—NH—$R_{17}$-D group in which $R_{17}$ is an alkylene and D is a quaternary ammonium group;
$A_1$ and $B_1$ represent divalent polymethylene groups comprising from 2 to 20 carbon atoms, which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and X⁻ denotes an anion derived from a mineral or organic acid;

it being understood that $A_1$, $R_{13}$ and $R_{15}$ can form, with the two nitrogen atoms to which they are attached, a piperazine ring;

in addition, if $A_1$ denotes a linear or branched, saturated or unsaturated alkylene or hydroxyalkylene radical, $B_1$ may also denote a group $(CH_2)_n$—CO-D-OC—$(CH_2)_n$— in which D denotes:

a) a glycol residue of formula —O—Z—O—, in which Z denotes a linear or branched hydrocarbon-based radical, or a group corresponding to one of the following formulae: —$(CH_2$—$CH_2$—$O)_x$—$CH_2$—$CH_2$—; —[$CH_2$—$CH(CH_3)$—$O]_y$—$CH_2$—$CH(CH_3)$—, in which x and y denote an integer from 1 to 4, representing a defined and unique degree of polymerization or any number from 1 to 4 representing an average degree of polymerization;

b) a bis-secondary diamine residue, such as a piperazine derivative;

c) a bis-primary diamine residue of formula: —NH—Y—NH—, where Y denotes a linear or branched hydrocarbon-based radical, or else the divalent radical —$CH_2$—$CH_2$—S—S—$CH_2$—$CH_2$—;

d) a ureylene group of formula: —NH—CO—NH—.

Preferably, X⁻ is an anion, such as chloride or bromide. These polymers have a number-average molar mass (Mn) generally of between 1000 and 100,000.

Mention may be made more particularly of polymers that are composed of repeating units corresponding to the formula:

$$\begin{array}{c} R_1 \\ | \\ -N^+ - (CH_2)_n - N^+ - (CH_2)_p - \\ | \quad X^- \quad | \quad X^- \\ R_2 \quad\quad R_4 \end{array} \quad (IV)$$

in which $R_1$, $R_2$, $R_3$ and $R_4$, which may be identical or different, denote an alkyl or hydroxyalkyl radical containing from 1 to 4 carbon atoms approximately, n and p are integers ranging from 2 to 20 approximately, and X⁻ is an anion derived from a mineral or organic acid.

A particularly preferred compound of formula (IV) is the one for which $R_1$, $R_2$, $R_3$ and $R_4$ represent a methyl radical and n=3, p=6 and X=Cl, known as Hexadimethrine chloride according to the INCI (CTFA) nomenclature.

(9) polyquaternary ammonium polymers comprising units of formula (V):

$$\begin{array}{c} R_{18} \quad\quad\quad\quad\quad\quad\quad\quad\quad\quad\quad R_{20} \\ | \quad\quad\quad\quad\quad\quad\quad\quad\quad\quad\quad\quad | \\ -N^+ - (CH_2)_r - NH - CO - (CH_2)_q - CO - NH - (CH_2)_s - N^+ - A - \\ X^- | \quad\quad\quad\quad\quad\quad\quad\quad\quad\quad\quad\quad\quad\quad\quad\quad X^- \quad | \\ R_{19} \quad\quad\quad\quad\quad\quad\quad\quad\quad\quad\quad\quad\quad\quad\quad R_{21} \end{array} \quad (V)$$

in which:

$R_{18}$, $R_{19}$, $R_{20}$ and $R_{21}$, which may be identical or different, represent a hydrogen atom or a methyl, ethyl, propyl, β-hydroxyethyl, β-hydroxypropyl or —$CH_2CH_2$ $(OCH_2CH_2)_p$OH radical, in which p is equal to 0 or to an integer between 1 and 6, with the proviso that $R_{18}$, $R_{19}$, $R_{20}$ and $R_{21}$ do not simultaneously represent a hydrogen atom, r and s, which may be identical or different, are integers between 1 and 6, q is equal to 0 or to an integer between 1 and 34, X⁻ denotes an anion such as a halide, A denotes a dihalide radical or preferably represents —$CH_2$—$CH_2$—O—$CH_2$—$CH_2$—. Examples that may be mentioned include the products Mirapol® A 15, Mirapol® AD1, Mirapol® AZ1 and Mirapol® 175 sold by the company Miranol.

(10) quaternary polymers of vinylpyrrolidone and of vinylimidazole, for instance the products sold under the names Luviquat® FC 905, FC 550 and FC 370 by the company BASF.

(11) polyamines such as Polyquart® H sold by Cognis, referred to under the name Polyethylene glycol (15) tallow polyamine in the CTFA dictionary.

(12) polymers comprising in their structure:

(a) one or more units corresponding to formula (A) below:

$$\begin{array}{c} -CH_2-CH- \\ | \\ NH_2 \end{array} \quad (A)$$

(b) optionally one or more units corresponding to formula (B) below:

$$\begin{array}{c} -CH_2-CH- \\ | \\ NH-C-H \\ \| \\ O \end{array} \quad (B)$$

In other words, these polymers may be chosen in particular from homopolymers or copolymers comprising one or more units derived from vinylamine and optionally one or more units derived from vinylformamide.

Preferably, these cationic polymers are chosen from polymers comprising, in their structure, from 5 mol % to 100 mol % of units corresponding to the formula (A) and from 0 to 95 mol % of units corresponding to the formula (B), preferably from 10 mol % to 100 mol % of units corresponding to the formula (A) and from 0 to 90 mol % of units corresponding to the formula (B).

These polymers may be obtained, for example, by partial hydrolysis of polyvinylformamide. This hydrolysis may take place in acidic or basic medium.

The weight-average molecular mass of said polymer, measured by light scattering, may range from 1000 to 3,000,000 g/mol, preferably from 10,000 to 1,000,000 and more particularly from 100,000 to 500,000 g/mol.

The cationic charge density of these polymers may range from 2 meq/g to meq/g, preferably from 2.5 to 15 and more particularly from 3.5 to 10 meq/g.

The polymers comprising units of formula (A) and optionally units of formula (B) are sold in particular under the Lupamin name by BASF, for instance, in a nonlimiting way, the products provided under the names Lupamin 9095, Lupamin 5095, Lupamin 1095, Lupamin 9030 (or Luviquat 9030) and Lupamin 9010.

Preferably, the cationic polymers are chosen from those of families (1), (2), (7) and (10) mentioned above.

Among the cationic polymers mentioned above, the ones that may preferably be used are cationic polysaccharides, in particular cationic celluloses and cationic galactomannan gums, and in particular quaternary cellulose ether derivatives such as the products sold under the name JR 400 by the company Amerchol, cationic cyclopolymers, in particular dimethyldiallylammonium salt (for example chloride) homopolymers or copolymers, sold under the names Merquat 100, Merquat 550 and Merquat S by the company Nalco, and homologs thereof of low weight-average molecular weights, quaternary polymers of vinylpyrrolidone and of vinylimidazole, optionally crosslinked homopolymers or copolymers of methacryloyloxy($C_1$-$C_4$)alkyltri($C_1$-$C_4$)alkylammonium salts, and mixtures thereof.

It is also possible to use amphoteric polymers, which may preferably be chosen from amphoteric polymers comprising the repetition of:

(i) one or more units derived from a (meth)acrylamide-type monomer, (ii) one or more units derived from a (meth)acrylamidoalkyltrialkylammonium-type monomer, and (iii) one or more units derived from a (meth)acrylic acid-type acid monomer.

Preferably, the units derived from a (meth)acrylamide-type monomer (i) are units of structure (Ia) below:

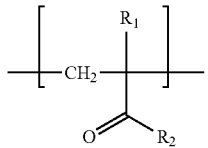

(Ia)

in which $R_1$ denotes H or $CH_3$ and $R_2$ is chosen from an amino, dimethylamino, tert-butylamino, dodecylamino and —NH—$CH_2$OH radical.

Preferably, said amphoteric polymer comprises the repetition of only one unit of formula (Ia).

The unit derived from a monomer of (meth)acrylamide type of formula (Ia) in which $R_1$ denotes H and $R_2$ is an amino radical ($NH_2$) is particularly preferred. It corresponds to the acrylamide monomer per se.

Preferably, the units resulting from a (meth)acrylamidoalkyltrialkylammonium-type monomer (ii) are units of structure (IIa) below:

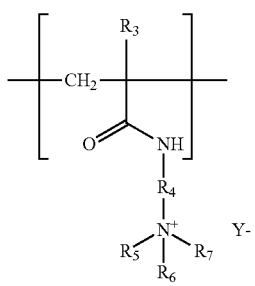

(IIa)

in which:

$R_3$ denotes H or $CH_3$, $R_4$ denotes a group $(CH_2)_k$ with k being an integer ranging from 1 to 6 and preferably from 2 to 4;

$R_5$, $R_6$, and $R_7$, which may be identical or different, each denote an alkyl group containing from 1 to 4 carbon atoms;

$Y^-$ is an anion such as bromide, chloride, acetate, borate, citrate, tartrate, bisulfate, bisulfite, sulfate or phosphate.

Preferably, said amphoteric polymer comprises the repetition of only one unit of formula (IIa).

Among these units derived from a (meth)acrylamidoalkyltrialkylammonium-type monomer of formula (IIa), the ones that are preferred are those derived from the methacrylamidopropyltrimethylammonium chloride monomer, for which $R_3$ denotes a methyl radical, k is equal to 3, $R_5$, $R_6$ and $R_7$ denote a methyl radical, and $Y^-$ denotes a chloride anion.

Preferably, the units derived from a (meth)acrylic acid-type monomer (iii) are units of formula (IIIa):

(IIIa)

in which $R_8$ denotes H or $CH_3$ and $R_9$ denotes a hydroxyl radical or an —NH—$C(CH_3)_2$—$CH_2$—$SO_3$H radical.

The preferred units of formula (IIIa) correspond to the acrylic acid, methacrylic acid and 2-acrylamido-2-methylpropanesulfonic acid monomers.

Preferably, the unit derived from a (meth)acrylic acid-type monomer of formula (IIIa) is that derived from acrylic acid, for which $R_8$ denotes a hydrogen atom and $R_9$ denotes a hydroxyl radical.

The (meth)acrylic acid-type acidic monomer(s) may be non-neutralized or partially or totally neutralized with an organic or mineral base.

Preferably, said amphoteric polymer comprises the repetition of only one unit of formula (IIIa).

According to a preferred embodiment of the invention, the amphoteric polymer(s) of this type comprise at least 30 mol % of units derived from a (meth)acrylamide-type monomer (i). Preferably, they comprise from 30 mol % to 70 mol % and more preferably from 40 mol % to 60 mol % of units derived from a (meth)acrylamide-type monomer.

The content of units derived from a (meth)acrylamidoalkyltrialkylammonium-type monomer (ii) may advantageously be from 10 mol % to 60 mol % and preferentially from 20 mol % to 55 mol %.

The content of units derived from a (meth)acrylic acid-type acidic monomer (iii) may advantageously be from 1 mol % to 20 mol % and preferentially from 5 mol % to 15 mol %.

According to a particularly preferred embodiment of the invention, the amphoteric polymer of this type comprises:

from 30 mol % to 70 mol % and more preferably from 40 mol % to 60 mol % of units derived from a (meth)acrylamide-type monomer (i), from 10 mol % to 60 mol % and preferentially from 20 mol % to 55 mol % of units derived from a (meth)acrylamidoalkyltrialkylammonium-type monomer (ii), and from 1 mol % to 20 mol % and preferentially from 5 mol % to 15 mol % of units derived from a (meth)acrylic acid-type monomer (iii).

Amphoteric polymers of this type may also comprise additional units, other than the units derived from a (meth) acrylamide-type monomer, a (meth)acrylamidoalkyltrialkylammonium-type monomer and a (meth)acrylic acid-type monomer as described above.

However, according to a preferred embodiment of the invention, said amphoteric polymers are constituted solely of units derived from monomers of (meth)acrylamide type (i), of (meth)acrylamidoalkyltrialkylammonium type (ii) and of (meth)acrylic acid type (iii).

Mention may be made, as an example of particularly preferred amphoteric polymers, of acrylamide/methacrylamidopropyltrimethylammonium chloride/acrylic acid terpolymers. Such polymers are listed in the CTFA International Cosmetic Ingredient Dictionary, 10th edition 2004, under the name Polyquaternium 53. Corresponding products are in particular sold under the names Merquat 2003 and Merquat 2003 PR by Nalco.

As another type of amphoteric polymer that may be used, mention may also be made of copolymers based on (meth) acrylic acid and on a dialkyldiallylammonium salt, and optionally on acrylamide or one of its derivatives, such as copolymers of (meth)acrylic acid and of dimethyldiallylammonium chloride. An example that may be mentioned is Merquat 280 sold by Nalco.

The composition according to the invention may comprise the cationic and/or amphoteric polymers in an amount of between 0.01% and 5% by weight, especially ranging from 0.05% to 3% by weight and preferentially from 0.1% to 2% by weight, relative to the total weight of the composition.

Silicone

The cosmetic composition according to the invention may also comprise one or more silicones, which are preferably liquid and volatile or nonvolatile.

The silicones that may be used may be soluble or insoluble in the composition according to the invention; they may be in the form of oil, wax, resin or gum; silicone oils and gums are preferred.

The volatile silicones may be chosen from those with a boiling point of between 60° C. and 260° C. (at atmospheric pressure) and more particularly from:

i) cyclic polydialkylsiloxanes comprising from 3 to 7 and preferably 4 to 5 silicon atoms, such as octamethylcyclotetrasiloxane and decamethylcyclopentasiloxane. Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia;

cyclocopolymers of the dimethylsiloxane/methylalkylsiloxane type having the chemical structure:

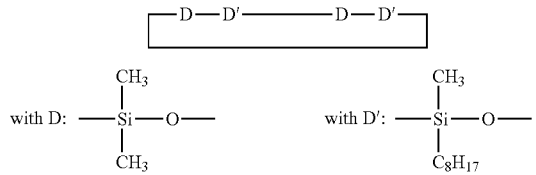

Mention may be made of Volatile Silicone FZ 3109 sold by the company Union Carbide;

mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;

ii) linear polydialkylsiloxanes containing 2 to 9 silicon atoms, which generally have a viscosity of less than or equal to $5 \times 10^{-6}$ m$^2$/s at 25° C., such as decamethyltetrasiloxane.

Among the nonvolatile silicones, mention may be made, alone or as a mixture, of polydialkylsiloxanes and especially polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes comprising in their structure one or more organofunctional groups, generally attached via a hydrocarbon-based group, and preferably chosen from aryl groups, amine groups, alkoxy groups and polyoxyethylene or polyoxypropylene groups.

The organomodified silicones may be polydiarylsiloxanes, especially polydiphenylsiloxanes, and polyalkylarylsiloxanes, functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes comprising:

polyethyleneoxy and/or polypropyleneoxy groups optionally comprising $C_6$-$C_{24}$ alkyl groups, such as dimethicone copolyols and especially those sold by the company Dow Corning under the name DC 1248 or the oils Silwet® L 722, L 7500, L 77 and L 711 from the company Union Carbide; or ($C_{12}$)alkylmethicone copolyols and especially those sold by the company Dow Corning under the name Q2 5200;

substituted or unsubstituted amine groups, in particular $C_1$-$C_4$ aminoalkyl groups; mention may be made of the products sold under the names GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in U.S. Pat. No. 4,957,732;

anionic groups of the carboxylic acid type, as described, for example, in EP 186 507, or of the alkylcarboxylic type, such as the product X-22-3701E from the company Shin-Etsu; or else of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP 342 834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:
- the Silbione® oils of the 47 and 70 047 series or the Mirasil® oils sold by Rhodia, such as, for example, the oil 70 047 V 500 000;
- the oils of the Mirasil® series sold by the company Rhodia;
- the oils of the 200 series from the company Dow Corning, such as DC200 with a viscosity of 60,000 mm²/s;
- the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly($C_1$-$C_{20}$)dialkylsiloxanes.

Products that may be used more particularly in accordance with the invention are mixtures such as:
- the mixtures formed from a polydimethylsiloxane hydroxylated at the chain end, or dimethiconol (CTFA), and from a cyclic polydimethylsiloxane, also known as cyclomethicone (CTFA), such as the product Q2 1401 sold by the company Dow Corning.

The polyalkylarylsiloxanes are particularly chosen from linear and/or branched polydimethyl/methylphenylsiloxanes and polydimethyl/diphenylsiloxanes with a viscosity ranging from $1 \times 10^{-5}$ to $5 \times 10^{-2}$ m²/s at 25° C.

Among these polyalkylarylsiloxanes, mention may be made of the products sold under the following names:
- the Silbione® oils of the 70 641 series from Rhodia;
- the oils of the Rhodorsil® 70 633 and 763 series from Rhodia;
- the oil Dow Corning 556 Cosmetic Grade Fluid from Dow Corning;
- the silicones of the PK series from Bayer, such as the product PK20;
- the silicones of the PN and PH series from Bayer, such as the products PN1000 and PH1000;
- certain oils of the SF series from General Electric, such as SF 1023, SF 1154, SF 1250 and SF 1265.

The cosmetic composition according to the invention may comprise said silicones in an amount ranging from 0.1% to 10% by weight and better still from 0.2% to 5% by weight relative to the total weight of the composition.

Thickener

The cosmetic composition according to the invention may also comprise one or more thickeners, preferably nonionic thickeners.

For the purposes of the present invention, the term "thickener" means a compound which, when introduced at 1% by weight in an aqueous solution or an aqueous-alcoholic solution containing 30% ethanol, and at pH 7, makes it possible to achieve a viscosity of at least 100 cps (centipoises) and preferably of at least 500 cps, at 25° C. and at a shear rate of 1 $s^{-1}$. This viscosity may be measured using a cone/plate viscometer (Haake R600 rheometer or the like).

The thickeners may be chosen from optionally oxyalkylenated fatty alcohols, fatty amides, oxyalkylenated fatty acid esters, and acrylic thickening polymers, and also mixtures thereof. They are preferably chosen from fatty amides and oxyalkylenated fatty acid esters.

The fatty alcohols preferably have the structure R—OH with R being a saturated or unsaturated, linear or branched hydrocarbon-based radical, comprising 8 to 40 carbon atoms, especially 8 to 30 carbon atoms, optionally substituted with one or more OH groups, preferably 1 to 2 OH groups; preferably, R is a $C_8$-$C_{40}$ and especially $C_{12}$-$C_{24}$ alkyl; or alternatively a $C_8$-$C_{40}$ and especially $C_{12}$-$C_{24}$ alkenyl. Mention may be made especially of the following compounds: lauryl alcohol, cetyl alcohol, stearyl alcohol, oleyl alcohol, behenyl alcohol, linoleyl alcohol, undecylenyl alcohol, palmitoleyl alcohol, arachidonyl alcohol and erucyl alcohol, and also mixtures thereof.

Advantageously, said fatty alcohols are solid at 25° C., i.e. they have a viscosity, measured with a rheometer (for example an R600 rheometer), at 25° C. and at a shear rate of 1 $s^{-1}$, of greater than or equal to 1 Pa·s.

Preferably, the fatty alcohols are chosen from stearyl alcohol, cetyl alcohol and mixtures thereof (cetylstearyl alcohol).

The term "fatty amide" means an amide comprising in its structure at least one hydrocarbon-based chain comprising at least 8 carbon atoms.

The fatty amides are more particularly chosen from compounds derived from an amide of alkanolamine and from a saturated or unsaturated, linear or branched fatty acid, comprising 8 to 30 carbon atoms, the alkanolamine and/or the fatty acid possibly being oxyalkylenated, preferably oxyethylenated, and comprising 1 to 50 mol of ethylene oxide (1-50 EO).

Preferably, the fatty amides are chosen from amides of $C_2$-$C_{10}$ alkanolamines and of $C_{14}$-$C_{30}$ fatty acids, and better still of $C_2$-$C_{10}$ alkanolamines and of $C_{14}$-$C_{22}$ fatty acids.

Mention may in particular be made of:
- the coconut (or coconut fatty acid) monoisopropanolamide, such as the product Empilan CLS from the company Huntsman,
- coconut (or coconut fatty acid) monoethanolamide, or cocamide MEA;
- soybean fatty acid diethanolamide, such as the product Comperlan® VOD from the company Cognis,
- oleic acid monoisopropanolamide, such as the product Witcamide® 61 from the company Witco,
- oleic acid diethanolamide, such as the product Mexanyl® GT from the company Chimex,
- myristic acid monoethanolamide, such as the product Comperlan® MM from the company Cognis,
- stearic acid ethanolamide or stearic acid monoethanolamide, such as the products Monamid® S and Monamid® 972 from the company Uniqema,
- linoleic acid diethanolamide, such as the product Purton® SFD from the company Zschimmer Schwarz,
- behenic acid monoethanolamide, such as the product Incromide® BEM from the company Croda,
- isostearic acid monoisopropanolamide, such as the product Witcamide® SPA from the company Witco,
- erucic acid diethanolamide, such as the product Erucic acid diethanolamide from the company Stearineries Dubois,
- ricinoleic acid monoethanolamide, such as the product Ricinoleic monoethanolamide from the company Stearineries Dubois,
- rapeseed fatty acid amide comprising 4 mol of EO, such as the product Amidet N from the company Kao.

The oxyalkylenated fatty acid esters may be chosen from oxyalkylenated derivatives of fatty acid esters or of fatty alcohol ethers.

Mention may be made most particularly of oxyalkylenated and especially oxyethylenated derivatives of esters of $C_6$-$C_{30}$ fatty acids or of ethers of $C_6$-$C_{30}$ fatty alcohols, and of polyols such as glycerol, sorbitol, glucose, pentaerythritol or polyethylene glycol, preferably polyethylene glycol, these derivatives preferably comprising 10 to 500 mol of ethylene oxide (EO), in particular 30 to 400 EO and preferably 40 to 300 mol of EO.

Mention may be made in particular of ethylene glycol stearate, polyethylene glycol distearate with 150 EO, glyceryl stearate with 200 EO such as the product Simulsol 220 TM® from SEPPIC, pentaerythrityl tetrastearate with 150 EO, such as the product Crothix® from Croda, methylglucose dioleate with 120 EO, such as the product Glucamate DOE-120 Vegetal® from the company Amerchol, sorbitan triisostearate with 160 EO, such as the product Rheodol TW IS399C from the company Kao Chemicals, and propylene glycol oleate with 55 EO, such as the product Antil 141 Liquid from the company Evonik Goldschmidt.

In particular, the oxyalkylenated fatty acid esters may correspond to the following formula:

$$R_1\text{---}CO\text{---}(X)_n\text{---}(OCH_2CH_2)_m\text{---}O\text{---}(CO)_p\text{---}R_2$$

in which:
$R_1$ is a linear or branched $C_9$-$C_{29}$ alkyl or alkenyl radical,
$R_1$ is a hydrogen atom or a linear or branched $C_9$-$C_{29}$ alkyl or alkenyl radical,
X is a linear or branched $C_1$-$C_4$ divalent alkylene radical, preferably of formula —$CH_2$—$CH(CH_3)$—;
n is 0 or 1, p is 0 or 1 and m is an integer ranging from 50 to 200.

Among the acrylic thickening polymers, the following are most particularly preferred:
crosslinked (meth)acrylic acid homopolymers, such as the products sold under the names Carbopol 980, 981, 954, 2984 and 5984 by the company Goodrich or the products sold under the names Synthalen M and Synthalen K by the company 3 VSA; and
crosslinked copolymers of (meth)acrylic acid and of a $C_1$-$C_6$ alkyl acrylate, and especially crosslinked copolymers of methacrylic acid and of ethyl acrylate or of acrylic acid and of ethyl acrylate, such as the products sold under the names Viscoatex 538C by the company Coatex, Aculyn 33 by the company Röhm & Haas, or Carbopol Aqua SF-1 by the company Noveon.

The cosmetic composition according to the invention may comprise the thickener(s) in an amount ranging from 0.01% to 10% by weight, better still from 0.05% to 8% by weight, even better still from 0.1% to 5% by weight and preferentially from 0.5% to 4% by weight, relative to the total weight of the composition.

Other Ingredients

The cosmetic composition according to the invention may be in any presentation form conventionally used and especially in the form of an aqueous, alcoholic or aqueous-alcoholic or oily solution or suspension; a solution or dispersion of the lotion or serum type; an emulsion, an aqueous or anhydrous gel, or any other cosmetic form.

The composition according to the invention is preferably aqueous and then comprises water at a concentration preferably ranging from 30% to 98% by weight, especially from 50% to 95% by weight and better still from 60% to 90% by weight, relative to the total weight of the composition.

The composition may also comprise one or more organic solvents that are liquid at 25° C. and 1 atm. and especially water-soluble, such as $C_1$-$C_6$ alcohols, especially $C_1$-$C_6$ aliphatic or aromatic monoalcohols; $C_3$-$C_7$ polyols such as glycerol; glycols such as butylene glycol, isoprene glycol or propylene glycol; and $C_3$-$C_7$ polyol ethers, which may thus be used alone or as a mixture with water. Advantageously, the organic solvent may be chosen from ethanol and isopropanol, and mixtures thereof.

The composition according to the invention may also comprise at least one common cosmetic ingredient, other than the compounds of the invention, chosen especially from plant, mineral, animal or synthetic oils; solid fatty substances and especially waxes, $C_8$-$C_{40}$ esters and $C_8$-$C_{40}$ acids; $C_8$-$C_{40}$ alcohols; cationic surfactants, anionic polymers; sunscreens; moisturizers; antidandruff agents; antioxidants; chelating agents; nacreous agents and opacifiers; plasticizers or coalescers; hydroxy acids; fillers; fragrances; basifying or acidifying agents; aldehydes, DHA; polymeric or non-polymeric thickeners, and especially associative polymers; preserving agents; sequestrants (EDTA and salts thereof); dyestuffs. The composition can, of course, comprise several cosmetic ingredients appearing in the above list. Those skilled in the art will take care to choose the ingredients included in the composition, and also the amounts thereof, such that they do not harm the properties of the compositions of the present invention.

The pH of the composition, if it is aqueous, is preferably between 4 and 7.5 and especially between 4.5 and 6.

The cosmetic composition may be rinsed off or left on after having been applied to the keratin materials; it is preferably rinsed off, after an optional leave-on time which may be a few minutes.

The cosmetic composition according to the invention especially finds a particularly advantageous application in the field of body and/or hair hygiene, especially for cleansing the hair and/or the scalp, and also for cleansing and/or removing makeup from bodily and/or facial skin.

It may thus constitute a shampoo or a shower gel, or alternatively a mask to be rinsed off.

A subject of the invention is also a cosmetic treatment process, especially for caring for and/or cleansing keratin materials, especially the hair, the scalp, bodily skin and/or facial skin, comprising the application to said keratin materials of a cosmetic composition according to the invention, optionally followed by rinsing, after an optional leave-on time.

The invention relates especially to a cosmetic process for cleansing soiling residues from human keratin materials, in which a composition according to the invention is applied to said keratin materials in the presence of water, it is massaged to form a foam, and the foam formed and the soiling residues are then removed by rinsing with water.

The invention is illustrated in greater detail in the examples that follow. In these examples, the viscosity is measured as indicated above (using a Haake Mars rheometer in cone-plate geometry, with a diameter of 60 mm/1°).

EXAMPLES

The below hair compositions of shampoo type (% by weight of active material AM) are prepared:

|  | Example 1 | Example 2 | Example 3 |
|---|---|---|---|
| Sodium $C_{14-16}$ olefin sulfonate (Bio-terge AS-40A from Stepan) | 12 | 7.5 | 15 |
| Disodium lauryl sulfosuccinate | 6 | — | — |
| Disodium laureth sulfosuccinate | — | 7.5 | — |
| Sodium lauroyl sarcosinate | — | — | 3 |

|  | | | |
|---|---|---|---|
| Cocamidopropyl betaine | 2 | 2 | 2 |
| Cocamide MEA | 0.5 | 2 | 1 |
| Polyquaternium-10 | 0.5 | 0.5 | 0.5 |
| PDMS 60 000 | 1.75 | 1.75 | 1.75 |
| Carbomer | 0.15 | 0.15 | 0.15 |
| NaCl | 1.25 | 0.45 | 0.85 |
| pH agent (citric acid, NaOH) | qs pH 5.3 | qs pH 5.3 | qs pH 5.3 |
| Water | qs 100% | qs 100% | qs 100% |
| Viscosity (mPa · s) | 7065 | 6000 | 6100 |
| Ratio (i)/(ii) | 2 | 1 | 5 |

|  | Example 4 | Example 5 | Example 6 |
|---|---|---|---|
| Sodium $C_{14-16}$ olefin sulfonate (Bio-terge AS-40A from Stepan) | 15 | 12 | 14 |
| Sodium lauroyl sarcosinate | 3 | 2.4 | 2 |
| Cocamidopropyl betaine | — | 2 | 2 |
| Cocobetaine | 2 | — | — |
| Cocamide MEA | 1 | 1 | 2 |
| Polyquaternium-10 | 0.5 | 0.5 | 0.5 |
| PDMS 60 000 | 1.75 | 1.75 | 1.75 |
| Carbomer | 0.15 | 0.15 | 0.15 |
| NaCl | 0.5 | 1.25 | 0.4 |
| pH agent (citric acid, NaOH) | qs pH 5.3 | qs pH 5.3 | qs pH 5.3 |
| Water | qs 100% | qs 100% | qs 100% |
| Viscosity (mPa · s) | 7000 | 7750 | 6300 |
| Ratio (i)/(ii) | 5 | 5 | 7 |

|  | Example 7 | Example 8 | Example 9 |
|---|---|---|---|
| Sodium $C_{14-16}$ olefin sulfonate (Bio-terge AS-40A from Stepan) | 9 | 8 | 8 |
| Sodium lauroyl sarcosinate | 4.5 | 4 | 4 |
| Cocamidopropyl betaine | 2 | 2 | 2 |
| Cocamide MEA | 1.5 | 2 | 1 |
| Polyquaternium-10 | 0.5 | 0.5 | 0.5 |
| PDMS 60 000 | 1.75 | 1.75 | 1.75 |
| Carbomer | 0.15 | 0.15 | 0.15 |
| NaCl | 1 | 0.4 | 1.2 |
| pH agent (citric acid, NaOH) | qs pH 5.3 | qs pH 5.3 | qs pH 5.3 |
| Water | qs 100% | qs 100% | qs 100% |
| Viscosity (mPa · s) | 6500 | 7600 | 6150 |
| Ratio (i)/(ii) | 2 | 2 | 2 |

|  | Example 10 | Example 11 | Example 12 |
|---|---|---|---|
| Sodium $C_{14-16}$ olefin sulfonate (Bio-terge AS-40A from Stepan) | 8 | 7 | 6 |
| Sodium lauroyl sarcosinate | 4 | 3.5 | 3 |
| Cocamidopropyl betaine | 2 | 2 | 2 |
| Cocamide MEA | 1.5 | 1.5 | 1.5 |
| Polyquaternium-10 | 0.5 | 0.5 | 0.5 |
| PDMS 60 000 | 1.75 | 1.75 | 1.75 |
| Carbomer | 0.15 | 0.15 | 0.15 |
| NaCl | 0.75 | 0.55 | 0.5 |
| pH agent (citric acid, NaOH) | qs pH 5.3 | qs pH 5.3 | qs pH 5.3 |
| Water | qs 100% | qs 100% | qs 100% |
| Viscosity (mPa · s) | 6700 | 6200 | 6800 |
| Ratio (i)/(ii) | 2 | 2 | 2 |

|  | Example 13 | Example 14 |
|---|---|---|
| Sodium $C_{14-16}$ olefin sulfonate (Bio-terge AS-40A from Stepan) | 10 | 7.5 |
| Sodium lauroyl sarcosinate | 5 | 7.5 |
| Cocamidopropyl betaine | 2 | 2 |
| Cocamide MEA | 2 | 2 |
| Polyquaternium-10 | 0.5 | 0.5 |
| PDMS 60 000 | 1.75 | 1.75 |
| Carbomer | 0.15 | 0.15 |
| NaCl | 0.6 | 0.5 |
| pH agent (citric acid, NaOH) | qs pH 5.3 | qs pH 5.3 |
| Water | qs 100% | qs 100% |
| Viscosity (mPa · s) | 5700 | 5270 |
| Ratio (i)/(ii) | 2 | 1 |

Stable detergent compositions are obtained, which exhibit good thickening, with a viscosity of at least 4 Pa·s, and a foaming effect, which may be used for cleansing the hair and lead to the production of good cosmetic properties for the hair.

The compositions exhibit good starting of foaming and generate an abundant foam of good quality: the foam in particular has a creamy texture and spreads easily over the whole head of hair.

Examples 4 and 7 were tested by a sensory panel of 10 trained consumers and compared with a sulfate-free commercial shampoo formulation.

The two examples according to the invention exhibit starting of foaming and foam abundance, firmness and persistence equivalent to those of the commercial product, even though these compositions according to the invention comprise much less anionic surfactant (between 10% and 30% less).

The invention claimed is:

1. A cosmetic composition comprising:
   (i) at least one linear α-olefin sulfonate,
   (ii) at least one anionic surfactant other than the compound (i), present in the composition in an amount ranging from 1% to 20% by weight, relative to the total weight of the composition; and
   (iii) at least one additional surfactant chosen from amphoteric surfactants, nonionic surfactants, or mixtures thereof,
   wherein the weight ratio of the amount of linear α-olefin sulfonate (i) to the amount of anionic surfactant (ii) other than the compound (i) ranges from about 1.5 to about 12,
   wherein (ii) the at least one anionic surfactant other than the compound (i) is chosen from:
   acylglycinates, acylsarcosinates, alkyl ether carboxylic acids, alkyl($C_6$-$C_{30}$ aryl) ether carboxylic acids, alkylamido ether carboxylic acids, or salts thereof, wherein the alkyl and/or acyl groups comprise from 6 to 30 carbon atoms; optionally polyoxyalkylenated or polyoxyethylenated and optionally comprising from 1 to 50 ethylene oxide units; and
   alkylamidesulfonates, alkylarylsulfonates, alkylsulfosuccinates, alkyl ether sulfosuccinates, alkylamide sulfosuccinates, alkylsulfoacetates, acylisethionates, or salts thereof, wherein the alkyl groups comprise from 6 to 30 carbon atoms; optionally polyoxyalkylenated or polyoxyethylenated and optionally comprising from 1 to 50 ethylene oxide units,
   wherein the composition does not comprise any anionic surfactants comprising sulfate groups.

2. The composition according to claim 1, wherein the linear α-olefin sulfonate is chosen from linear alkene sulfonates, linear hydroxyalkane sulfonates, or mixtures thereof.

3. The composition according to claim 2, wherein the linear alkene sulfonate is represented by the following formula:

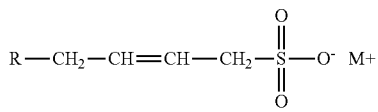

wherein:
R is chosen from a saturated linear alkyl radical comprising from 4 to 20 carbon atoms; and M is a cosmetically acceptable cation chosen from an ammonium cation, cations derived from alkali metals or alkaline-earth metals, cations derived from organic amines, cations derived from alkanolamines, Na+, or K+.

4. The composition according to claim 2, wherein the linear α-olefin sulfonate is chosen from linear alkene sulfonates of formula (A), linear hydroxyalkane sulfonates of formula (B), or mixtures thereof:

(A) R—CH$_2$—CH═CH—(CH$_2$)$_n$—SO$_3$M wherein:
R is chosen from a saturated linear alkyl radical comprising from 4 to 30 carbon atoms;
n is an integer ranging from 0 to 10; and
M is a cosmetically acceptable cation chosen from an ammonium cation, cations derived from alkali metals or alkaline-earth metals, cations derived from organic amines, cations derived from alkanolamines, Na+, or K+;

(B) R'—CH$_2$—CH(OH)—CH$_2$—(CH$_2$)$_{n'}$—SO$_3$M' wherein:
R' is chosen from a saturated linear alkyl radical comprising from 4 to 30 carbon atoms;
n' is an integer ranging from 0 to 10; and
M' is a cosmetically acceptable cation chosen from an ammonium cation, cations derived from alkali metals or alkaline-earth metals, cations derived from organic amines, cations derived from alkanolamines, Na+, or K+.

5. The composition according to claim 2, wherein the linear hydroxyalkane sulfonate is represented by the following formula:

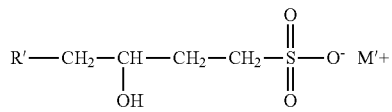

wherein:
R' is chosen from a saturated linear alkyl radical comprising from 4 to 20 carbon atoms; and
M' is a cosmetically acceptable cation chosen from an ammonium cation, cations derived from alkali metals or alkaline-earth metals, cations derived from organic amines, cations derived from alkanolamines, Na+, or K+.

6. The composition according to claim 1, wherein:
the linear α-olefin sulfonate is chosen from linear α-olefin sulfonates comprising 8 to 28 carbon atoms; and
the linear α-olefin sulfonate has a cation chosen from cations derived from alkali metals, sodium cations, or mixtures thereof.

7. The composition according to claim 1, wherein the total amount of linear α-olefin sulfonate ranges from about 1% to about 20% by weight, relative to the total weight of the cosmetic composition.

8. The composition according to claim 1, wherein the anionic surfactant other than the compound (i) is chosen from:
C$_6$-C$_{24}$ sarcosinates, C$_{12}$-C$_{20}$ sarcosinates, palm itoylsarcosinates, lauroylsarcosinates, sodium palm itoylsarcosinate, or sodium lauroylsarcosinate;
C$_6$-C$_{24}$ acylglycinates or C$_{12}$-C$_{20}$ acylglycinates;
(C$_6$-C$_{24}$)alkyl ether carboxylates or (C$_{12}$-C$_{20}$)alkyl ether carboxylates;
polyoxyalkylenated (C$_6$-C$_{24}$)alkyl amido ether carboxylic acids or polyoxyalkylenated (C$_6$-C$_{24}$)alkyl amido ether carboxylic acids comprising from 2 to 50 ethylene oxide groups;
C$_6$-C$_{24}$ alkylsulfosuccinates, C$_{12}$-C$_{20}$ alkylsulfosuccinates, or laurylsulfosuccinates;
C$_6$-C$_{24}$ alkylethersulfosuccinates, C$_{12}$-C$_{20}$ alkylethersulfosuccinates, or laurylsulfosuccinates, which are optionally oxyethylenated;
(C$_6$-C$_{24}$)acylisethionates, (C$_{12}$-C$_{18}$)acylisethionates, or cocoylisethionates; or
C$_6$-C$_{24}$ alkylsulfoacetates or C$_{12}$-C$_{20}$ alkylsulfoacetates.

9. The composition according to claim 1, wherein the total amount of anionic surfactant other than the compound (i) ranges from about 1.5% to about 15% by weight, relative to the total weight of the composition.

10. The composition according to claim 1, further comprising at least one additional surfactant chosen from nonionic surfactants, amphoteric surfactants; or:
alcohols, α-diols, or (C$_{1-20}$)alkylphenols, these compounds being polyethoxylated and/or polypropoxylated and/or polyglycerolated, the number of ethylene oxide and/or propylene oxide groups optionally ranging from 1 to 100, and the number of glycerol groups optionally ranging from 2 to 30; these compounds optionally comprising at least one fatty chain comprising from 8 to 30 carbon atoms;
condensates of ethylene oxide or of propylene oxide with fatty alcohols;
polyethoxylated fatty amides, polyethoxylated fatty amides having from 2 to 30 ethylene oxide units, polyglycerolated fatty amides comprising on average from 1 to 5 or from 1.5 to 4 glycerol groups; C$_8$-C$_{30}$ fatty acid alkanolam ides, C$_8$-C$_{30}$ fatty acid monoalkanolam ides, C$_8$-C$_{30}$ fatty acid monoethanolam ides, or C$_8$-C$_{30}$ fatty acid monoisopropanolam ides; ethoxylated fatty acid esters of sorbitan optionally containing from 2 to 40 ethylene oxide units, fatty acid esters of sucrose, polyoxyalkylenated or polyoxyethylenated fatty acid esters containing from 2 to 150 mol of ethylene oxide, oxyethylenated plant oils, N—(C$_{6-24}$ alkyl)glucamine derivatives, amine oxides, (C$_{10-14}$ alkyl)amine oxides, or N—(C$_{10-14}$ acyl)aminopropylmorpholine oxides;
nonionic surfactants of alkylpolyglycoside type, or compounds represented by the following general formula: R$_1$O—(R$_2$O)$_t$-(G)$_v$ wherein:
R$_1$ is chosen from a linear or branched alkyl or alkenyl radical comprising 6 to 24 carbon atoms or 8 to 18 carbon atoms, or an alkylphenyl radical whose linear or branched alkyl radical comprises 6 to 24 carbon atoms or 8 to 18 carbon atoms;
R$_2$ represents an alkylene radical comprising 2 to 4 carbon atoms,
G represents a sugar unit comprising 5 to 6 carbon atoms,
t denotes a value ranging from 0 to 10,
v denotes a value ranging from 1 to 15;
(C$_8$-C$_{20}$)alkylbetaines, sulfobetaines, (C$_8$-C$_{20}$)alkylsulfobetaines, (C$_8$-C$_{20}$)alkylamido(C$_1$-C$_6$)alkylbetaines, cocamidopropylbetaine, (C$_8$-C$_{20}$)alkylamido (C$_1$-C$_6$)alkylsulfobetaines, or mixtures thereof;

optionally quaternized secondary or tertiary aliphatic amine derivatives represented by formula (A1) or formula (A2):

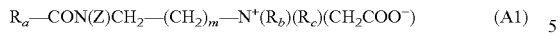

$R_a$—CON(Z)CH$_2$—(CH$_2$)$_m$—N$^+$(R$_b$)(R$_c$)(CH$_2$COO$^-$)  (A1)

wherein:
$R_a$ represents a $C_{10}$-$C_{30}$ alkyl or alkenyl group derived from an acid $R_a$—COOH, or a heptyl, nonyl, or undecyl group,
$R_b$ represents a β-hydroxyethyl group,
$R_c$ represents a carboxymethyl group;
m is equal to 0, 1, or 2,
Z is chosen from a hydrogen atom, a hydroxyethyl group, or a carboxymethyl group,

$R_{a'}$—CON(Z)CH$_2$—(CH$_2$)$_{m'}$—N(B)(B')  (A2)

wherein:
B represents —CH$_2$CH$_2$OX', with X' representing —CH$_2$—COOH, CH$_2$—COOZ', —CH$_2$CH$_2$—COOH, —CH$_2$CH$_2$—COOZ', or a hydrogen atom,
B' represents —(CH$_2$)z-Y', with z=1 or 2, and Y' is chosen from —COON, —COOZ', —CH$_2$—CHOH—SO$_3$H, or —CH$_2$—CHOH—SO$_3$Z',
m' is equal to 0, 1, or 2,
Z represents a hydrogen atom, a hydroxyethyl group, or a carboxymethyl group,
Z' represents an ion derived from an alkali metal, an alkaline-earth metal, sodium, potassium, or magnesium; an ammonium ion; or an ion derived from an organic amine, an amino alcohol, monoethanolamine, diethanolamine, triethanolamine, monoisopropanolamine, diisopropanolamine triisopropanolamine, 2-amino-2-methyl-1-propanol, 2-amino-2-methyl-1,3-propanediol, or tris(hydroxymethyl)aminomethane,
$R_{a'}$ is chosen from a $C_{10}$-$C_{30}$ alkyl or alkenyl group of an acid $R_a$COOH optionally present in hydrolyzed linseed oil or coconut oil, an alkyl group, a $C_{17}$ alkyl group, a $C_{17}$ alkyl group in iso form, or an unsaturated $C_{17}$ group; or
compounds represented by formula (A3):

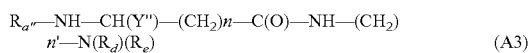

$R_{a''}$—NH—CH(Y'')—(CH$_2$)n—C(O)—NH—(CH$_2$)
n'—N(R$_d$)(R$_e$)  (A3)

wherein:
$R_{a''}$ represents a $C_{10}$-$C_{30}$ alkyl or alkenyl group of an acid $R_{a''}$—C(O)OH, which is optionally present in hydrolyzed linseed oil or coconut oil;
Y'' is chosen from C(O)OH, —C(O)OZ'', —CH$_2$—CH(OH)—SO$_3$H, or —CH$_2$—CH(OH)—SO$_3$—Z'', wherein Z'' is chosen from a cation resulting from an alkali metal, alkaline-earth metal, sodium, an ammonium ion, or an ion resulting from an organic amine;
$R_d$ and $R_e$, independently of each other, represent a $C_1$-$C_4$ alkyl or hydroxyalkyl radical; and
n and n', independently of each other, denote an integer ranging from 1 to 3.

11. The composition according to claim 10, wherein the total amount of additional surfactant ranges from about 0.5% to about 20% by weight, relative to the total weight of the composition.

12. The composition according to claim 1, further comprising at least one nonionic surfactant and at least one amphoteric surfactant, wherein:
the nonionic surfactant may be chosen from ($C_6$-$_{24}$ alkyl) polyglycosides, ($C_{8-18}$ alkyl)polyglycosides, ethoxylated $C_8$-$C_{30}$ fatty acid esters of sorbitan, polyethoxylated $C_8$-$C_{30}$ fatty alcohols and polyoxyethylenated $C_8$-$C_{30}$ fatty acid esters, these compounds optionally containing from 2 to 150 mol of ethylene oxide, $C_8$-$C_{30}$ fatty acid alkanolam ides, $C_8$-$C_{30}$ fatty acid monoalkanolam ides, $C_8$-$C_{30}$ fatty acid monoethanolam ides or monoisopropanolam ides, or mixtures thereof; and/or
the amphoteric surfactant may be chosen from ($C_8$-$C_{20}$) alkylbetaines, ($C_8$-$C_{20}$)alkylamido($C_1$-$C_6$)alkylbetaines, ($C_8$-$C_{20}$)alkylamphoacetates and ($C_8$-$C_{20}$)alkylamphodiacetates, or mixtures thereof.

13. The composition as according to claim 1, further comprising at least one polymer chosen from amphoteric or cationic polymers, or mixtures thereof, in an amount ranging from about 0.01% to about 5% by weight, relative to the total weight of the composition.

14. The composition according to claim 1, further comprising at least one silicone, which are optionally liquid, volatile, or nonvolatile; wherein the total amount of silicone ranges from about 0.1% to about 10% by weight, relative to the total weight of the composition.

15. The composition according to claim 1, further comprising water in an amount ranging from about 30% to about 98% by weight, relative to the total weight of the composition.

16. The composition according to claim 1, further comprising at least one thickener, which is optionally chosen from nonionic thickeners, optionally oxyalkylenated fatty alcohols, fatty amides, oxyalkylenated fatty acid esters, acrylic thickening polymers, or mixtures thereof.

17. A cosmetic treatment process for caring for and/or cleansing keratin materials, the method comprising:
applying to the keratin materials a cosmetic composition comprising:
(i) at least one linear α-olefin sulfonate,
(ii) at least one anionic surfactant other than the compound (i), present in the composition in an amount ranging from 1% to 20% by weight, relative to the total weight of the composition; and
(iii) at least one additional surfactant chosen from amphoteric surfactants, nonionic surfactants, or mixtures thereof,
wherein the weight ratio of the amount of linear α-olefin sulfonate (i) to the amount of anionic surfactant (ii) other than the compound (i) ranges from about 1.5 to about 12,
wherein (ii) the at least one anionic surfactant other than the compound (i) is chosen from:
acylglycinates, acylsarcosinates, alkyl ether carboxylic acids, alkyl($C_6$-$C_{30}$ aryl) ether carboxylic acids, alkylamido ether carboxylic acids, or salts thereof, wherein the alkyl and/or acyl groups comprise from 6 to 30 carbon atoms; optionally polyoxyalkylenated or polyoxyethylenated and optionally comprising from 1 to 50 ethylene oxide units; and
alkylamidesulfonates, alkylarylsulfonates, alkylsulfosuccinates, alkyl ether sulfosuccinates, alkylamide sulfosuccinates, alkylsulfoacetates, acylisethionates, or salts thereof, wherein the alkyl groups comprise from 6 to 30 carbon atoms; optionally polyoxyalkylenated or polyoxyethylenated and optionally comprising from 1 to 50 ethylene oxide units,
wherein the composition does not comprise any anionic surfactants comprising sulfate groups; and
optionally rinsing the cosmetic composition from the keratin materials after an optional leave-on time.

18. A cosmetic process for cleansing soiling residues from human keratin materials, the method comprising:
  applying to the keratin materials in the presence of water a cosmetic composition comprising:
    (i) at least one linear α-olefin sulfonate,
    (ii) at least one anionic surfactant other than the compound (i), present in the composition in an amount ranging from 1% to 20% by weight, relative to the total weight of the composition; and
    (iii) at least one additional surfactant chosen from amphoteric surfactants, nonionic surfactants, or mixtures thereof,
  wherein the weight ratio of the amount of linear α-olefin sulfonate (i) to the amount of anionic surfactant (ii) other than the compound (i) ranges from about 1.5 to about 12,
  wherein (ii) the at least one anionic surfactant other than the compound (i) is chosen from:
  acylglycinates, acylsarcosinates, alkyl ether carboxylic acids, alkyl($C_6$-$C_{30}$ aryl) ether carboxylic acids, alkylamido ether carboxylic acids, or salts thereof, wherein the alkyl and/or acyl groups comprise from 6 to 30 carbon atoms; optionally polyoxyalkylenated or polyoxyethylenated and optionally comprising from 1 to 50 ethylene oxide units; and
  alkylamidesulfonates, alkylarylsulfonates, alkylsulfosuccinates, alkyl ether sulfosuccinates, alkylamide sulfosuccinates, alkylsulfoacetates, acylisethionates, or salts thereof, wherein the alkyl groups comprise from 6 to 30 carbon atoms; optionally polyoxyalkylenated or polyoxyethylenated and optionally comprising from 1 to 50 ethylene oxide units,
    wherein the composition does not comprise any anionic surfactants comprising sulfate groups;
  massaging the keratin materials to form a foam; and
  removing the foam formed and the soiling residues from the keratin materials by rinsing with water.

* * * * *